US012571750B2

(12) United States Patent (10) Patent No.: US 12,571,750 B2
Gregg (45) Date of Patent: Mar. 10, 2026

(54) THERMAL CONDUCTIVITY PROBE

(71) Applicant: Seas Geosciences, LLC, Signal Hill, CA (US)

(72) Inventor: John Gregg, Signal Hill, CA (US)

(73) Assignee: Seas Geosciences, LLC, Signal Hill, CA (US)

( * ) Notice: Subject to any disclaimer, the term of this patent is extended or adjusted under 35 U.S.C. 154(b) by 0 days.

(21) Appl. No.: 18/635,902

(22) Filed: Apr. 15, 2024

(65) Prior Publication Data

US 2024/0255451 A1 Aug. 1, 2024

Related U.S. Application Data

(63) Continuation of application No. 18/207,118, filed on Jun. 7, 2023.

(60) Provisional application No. 63/460,267, filed on Apr. 18, 2023, provisional application No. 63/330,776, filed on Apr. 14, 2022.

(51) Int. Cl.
*G01N 25/18* (2006.01)
*G01N 33/24* (2006.01)

(52) U.S. Cl.
CPC ............. *G01N 25/18* (2013.01); *G01N 33/24* (2013.01)

(58) Field of Classification Search
CPC .......... G01N 25/18; G01N 33/24; G01N 9/00; G01N 21/31; G01N 15/0826; E02D 1/00; E02D 1/022; E02D 1/027
See application file for complete search history.

(56) References Cited

U.S. PATENT DOCUMENTS

| | | | |
|---|---|---|---|
| 3,165,915 A | 1/1965 | Parker | |
| 3,263,485 A * | 8/1966 | Mahmoodi | G01N 25/18 |
| | | | 374/112 |
| 4,933,877 A | 6/1990 | Danko | |
| 5,044,764 A | 9/1991 | Aoki et al. | |
| 5,343,002 A | 8/1994 | Gremillion | |
| 6,695,075 B2 | 2/2004 | Beeker et al. | |
| 9,182,364 B1 | 11/2015 | Condie et al. | |
| 9,637,978 B2 * | 5/2017 | Holloway | E21B 7/12 |
| 10,180,360 B1 * | 1/2019 | Naranjo | G01K 1/026 |
| 2007/0006639 A1 * | 1/2007 | Sasanuma | G01N 25/18 |
| | | | 73/53.01 |
| 2011/0106451 A1 * | 5/2011 | Christy | G01N 21/359 |
| | | | 702/5 |

(Continued)

FOREIGN PATENT DOCUMENTS

| | | |
|---|---|---|
| AU | 2020102910 A4 * | 12/2020 |
| CN | 206362733 U * | 7/2017 |

(Continued)

OTHER PUBLICATIONS

PCT International Search Report; International App. No.: PCT/US2023/025014; Oct. 9, 2023; pp. 1-7.

(Continued)

*Primary Examiner* — John E Breene
*Assistant Examiner* — Janice M Soto

(57) ABSTRACT

This invention relates generally to a thermal conductivity probe. In one embodiment, a thermal conductivity probe includes, but is not limited to, at least one heating element, at least one thermal insulator, and at least one thermistor thermally isolated from the at least one heating element by the at least one thermal insulator.

21 Claims, 4 Drawing Sheets

(56)　　　　　References Cited

U.S. PATENT DOCUMENTS

| 2011/0134958 | A1 | | 6/2011 | Arora | |
|---|---|---|---|---|---|
| 2017/0045489 | A1 | | 2/2017 | Sauder | |
| 2023/0105228 | A1 | * | 4/2023 | Ito | G01N 25/18 374/44 |

FOREIGN PATENT DOCUMENTS

| CN | 107 727 687 | B | | 9/2020 |
|---|---|---|---|---|
| CN | 113186891 | A | * | 7/2021 |
| DE | 10 2011 001153 | A1 | | 9/2012 |
| DE | 10 2016 110 352 | A1 | | 12/2016 |
| DE | 112015002036 | B4 | | 6/2019 |
| EP | 0 429 130 | B1 | | 11/1990 |
| EP | 1154076 | B1 | | 3/2005 |
| NL | 9001081 | A | | 12/1991 |
| NL | 1005899 | C2 | | 10/1998 |
| NL | 1010059 | C2 | | 3/2000 |
| NL | 1015147 | C2 | | 11/2001 |
| NL | 1025239 | C2 | | 7/2005 |
| NL | 1029507 | C2 | | 3/2006 |
| NL | 1032469 | C2 | | 3/2008 |
| NL | 2016592 | B1 | | 11/2017 |
| WO | WO 2016/155383 | A1 | | 10/2016 |
| WO | WO 2021/228351 | A1 | | 11/2021 |
| WO | WO 2023/201123 | A1 | | 10/2023 |

OTHER PUBLICATIONS

Bording Thue S et al: "Determination of thermal properties of materials by Monte Carlo inversion of pulsed needle probe data", International Journal of Heat and Mass Transfer, vol. 133, pp. 154-165, XP085600831, ISSN: 0017-9310, DOI: 10.1016/J. 1JHEATMASSTRANSFER.2018.12.104.

Michael M Harris et al: "Sensing shallow seafloor and sediment properties, recent history", Oceans 2008, IEEE, Piscataway, NJ, USA, Sep. 15, 2008 (Sep. 15, 2008), pp. 1-11, XP031548124, ISBN: 978-1-4244-2619-5.

* cited by examiner

Figure 1

THERMAL CONDUCTIVITY PROBE

PRIORITY CLAIM

This application is a continuation of U.S. non-provisional patent application Ser. No. 18/207,118 filed Jun. 7, 2023, titled Thermal Conductivity Probe, which application is a non-provisional patent application of (i) U.S. provisional patent application 63/330,776 filed Apr. 14, 2022, titled Thermal Conductivity Probe and (ii) U.S. provisional patent application 63/460,267 filed Apr. 18, 2023, titled Thermal Conductivity Probe.

This application claims the benefit of and/or priority to each of the foregoing patent applications and any and all parent, grandparent, and great-grandparent applications thereof. The foregoing patent applications are incorporated by reference in their entirety as if fully set forth herein.

FIELD OF THE INVENTION

This disclosure relates generally to a thermal conductivity probe.

BACKGROUND

There is a growing need to accurately and easily calculate energy loss through various sediment types for power lines embedded below the ground surface. With embedded subsurface current transmission lines, energy loss is directly related to heat loss through the surrounding strata. Thus, in order to quantify energy loss, and determine the transmission efficiency, systems and methods for measuring the thermal conductivity of soil would be useful and are disclosed herein.

SUMMARY

Embodiments disclosed herein relate generally to a thermal conductivity probe. In one embodiment, a thermal conductivity probe includes, but is not limited to, at least one heating element, at least one thermal insulator, and at least one thermistor thermally isolated from the at least one heating element by the at least one thermal insulator.

In another embodiment, an attachment that couples to a cone penetration device (CPT) includes, but is not limited to, at least one heating element, at least one thermal insulator, at least one thermistor thermally isolated from the at least one heating element by the at least one thermal insulator, and a threaded member configured to removably couple to a CPT.

In a further embodiment, a thermal conductivity system includes, but is not limited to, at least one heating element, at least one thermal insulator, at least one thermistor thermally isolated from the at least one heating element by the at least one thermal insulator, and at least one processor configured to perform operations including at least control the at least one heating element, and measure temperature using the at least one thermistor over time.

BRIEF DESCRIPTION OF THE DRAWINGS

Embodiments are described in detail below with reference to the following drawings.

FIG. 1 is a perspective view of a thermal conductivity probe, in accordance with an embodiment of the invention.

DETAILED DESCRIPTION

Figure 2:
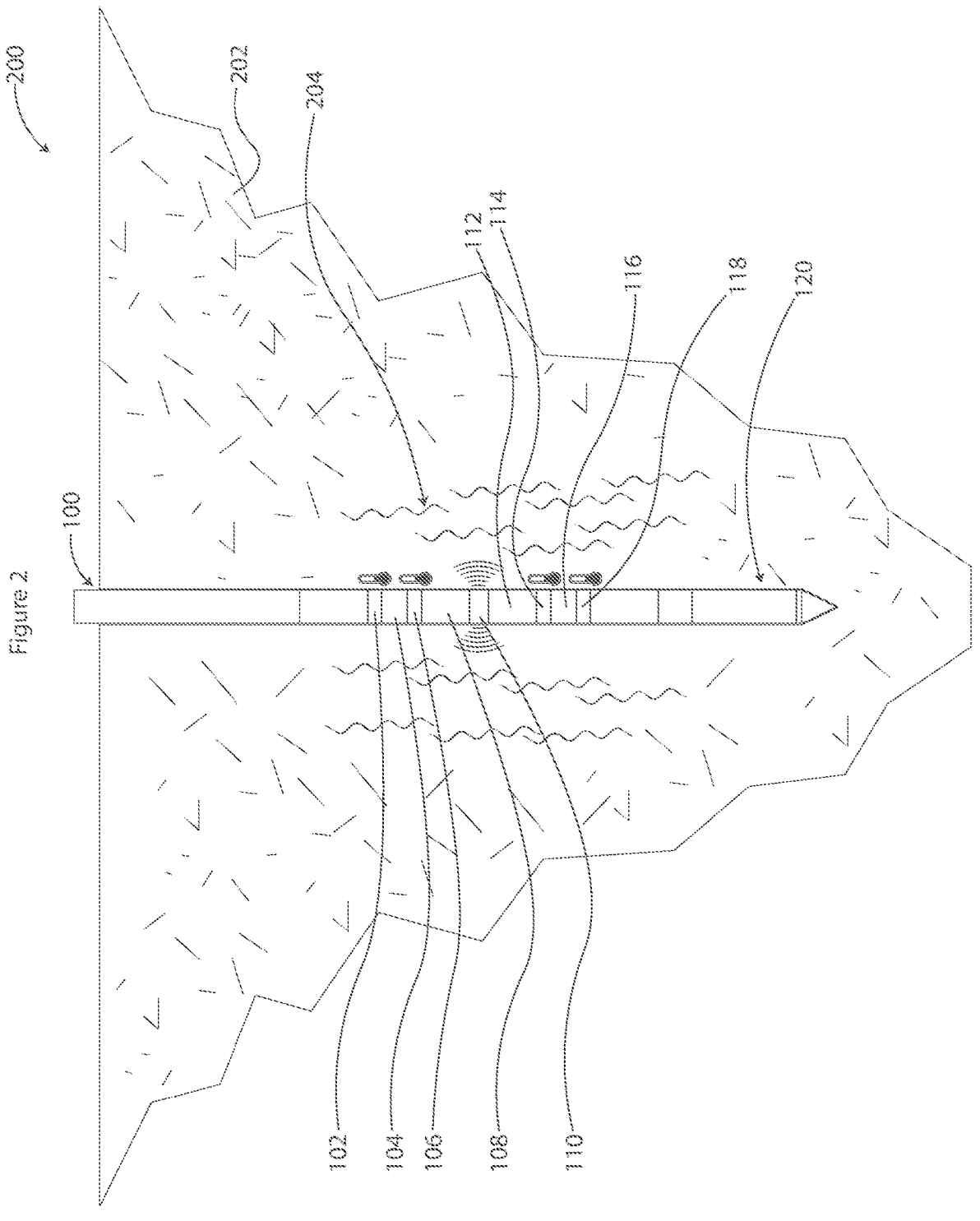
FIG. 2 is an environmental view of a thermal conductivity probe, in accordance with an embodiment of the invention.

This disclosure relates generally to a thermal conductivity probe. Certain embodiments are set forth in the following description and in FIGS. 1-4 to provide a thorough understanding of such embodiments.

Figure 1:
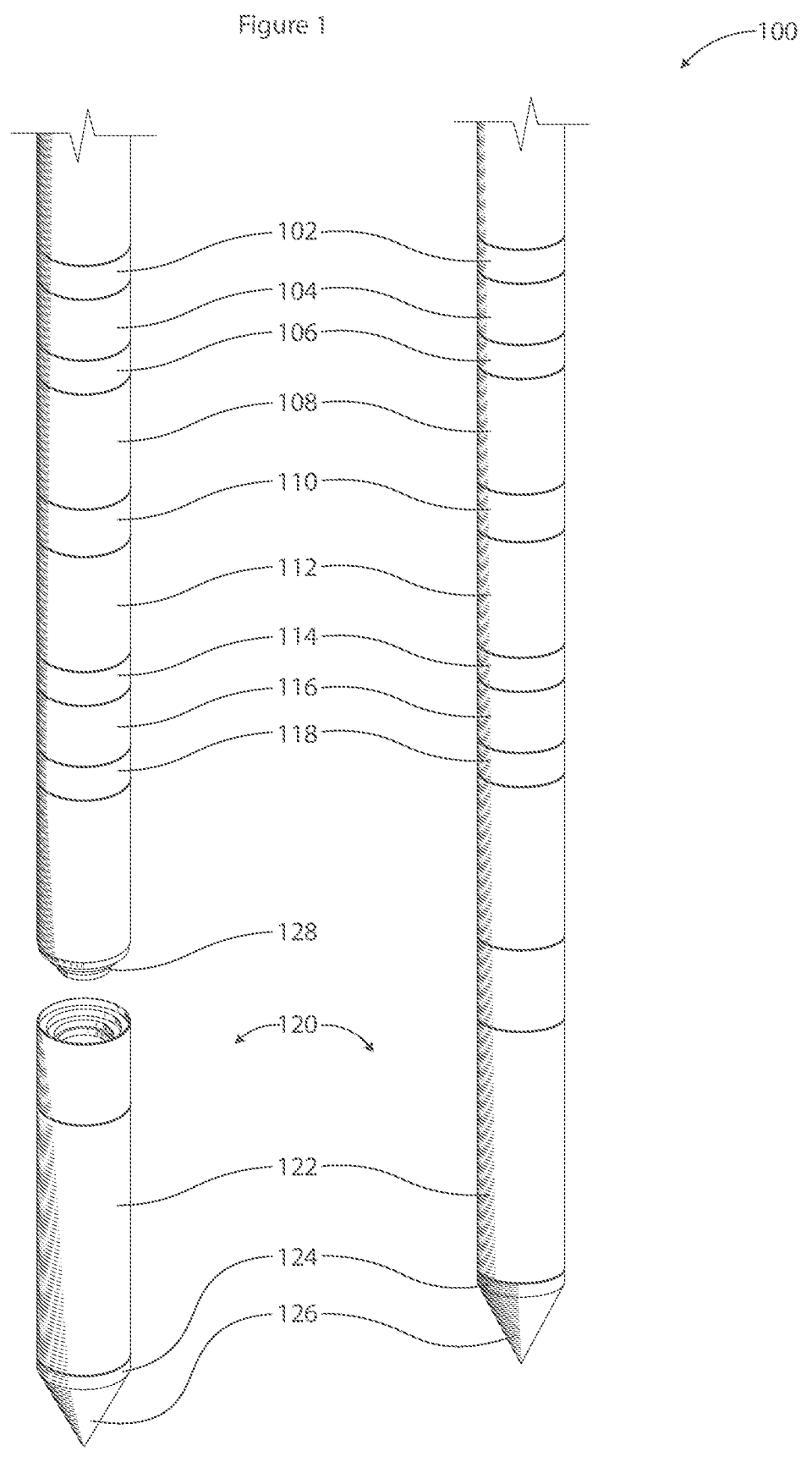

FIG. 1 is a perspective view of a thermal conductivity probe, in accordance with an embodiment of the invention. In one embodiment, a thermal conductivity probe 100 includes, but is not limited to, at least one heating element 110, at least one thermal insulator 108; and at least one thermistor 106 thermally isolated from the at least one heating element 110 by the at least one thermal insulator 108. In certain embodiments, the thermal conductivity probe 100 further includes thermistor 102, thermal insulator 104, thermal insulator 112, thermistor 114, thermal insulator 116, and thermistor 118. In further embodiments, the thermal conductivity probe 100 further includes CPTu 120 with friction sleeve 122, pore pressure element 124, and cone tip 126. Various embodiments of the thermal conductivity probe 100 include various combinations of the foregoing elements, as further disclosed herein.

The knowledge of thermal conductivity in soil is important for several applications, including designing underground structures, determining heat loss and energy transmission efficiency of underground subsurface power and data lines, assessing heat transfer in geothermal systems, predicting soil temperature profiles, and understanding the energy balance in agricultural systems.

The thermal conductivity probe 100 provides a tool to measure in situ thermal conductivity through a subsurface soil profile. The thermal conductivity probe 100 is designed to fit behind a cone penetration device CPTu 120 that will measure the thermal transmission and enable plotting of the result along with other CPT data such as depth, tip and sleeve resistance, pore pressure and inclination. The thermal conductivity probe 100 is approximately 10-100 mm in diameter (e.g., 36 mm) and 100-1000 mm in length (e.g., 425 mm). In operation, the thermal conductivity probe 100 and CPTu 120 are pushed into the soil with traditional CPT deployment frames. Typically, these deployment frames consist of a pair of hydraulic cylinders that can exert up to 20 metric tons of force. As the thermal conductivity probe 100 and CPT 120 are pushed to a depth of interest, typically 1-10 m (e.g., 2 m) below ground surface, the heating element 110 is energized and begins to heat the surrounding soil. The element reaches a prescribed temperature, such as between 50° C.-200° C. (e.g., 90° C.) and maintains that temperature for a prescribed length of time, such as 1 min-60 min, for example. The time may vary and is dependent on the hydraulic conductivity and density of the soil. Specifically, when the thermistor 106 reads 1° C.-20° C. (e.g., 5° C.) above ambient temperature, the heating element 110 is turned off. The decay in temperature as measured using thermistor 106 is then plotted against time and a temperature decay index is thus derived. This temperature decay index is then used to calculate heat loss along the transmission line.

In certain embodiments, the thermistor 102, thermal insulator 104, thermal insulator 112, thermistor 114, thermal insulator 116, and thermistor 118 are provided. When the thermistors 102 and/or 118 read 1° C.-20° C. (e.g., 5° C.) above ambient temperature, the heating element 110 is turned off. The decay in temperature is then plotted against time for each of the four thermistors 102, 106, 114, and 118. The slope of the four temperature decay curves is then averaged, and a mean temperature decay index is derived. This factor is then used to calculate heat loss along the transmission line.

In a further embodiment, the thermal conductivity probe 100 includes, but is not limited to a plurality of thermistors thermally isolated from the at least one heating element 110. The plurality of thermistors can include thermistor 106 thermally isolated from heating element 110 by thermal insulator 108 and thermistor 102 thermally isolated from thermistor 106 by thermal insulator 104. Further, the plurality of thermistors can include thermistor 114 thermally isolated from the heating element 110 by thermal insulator 112 and thermistor 118 thermally isolated from thermistor 114 by thermal insulator 116. Alternatively, the plurality of thermistors can include thermistor 106 thermally isolated from heating element 110 by thermal insulation 108 and thermistor 114 thermally isolated from heating element 110 by thermal insulator 112.

The heating element disposed about a circumference along a section length of the thermal conductivity probe. For instance, the heating element can be a section of approximately 5 mm-100 mm (e.g., 45 mm) in length and 10-100 mm in diameter (e.g., 36 mm) with a wall thickness of approximately 1 mm-50 mm. In certain embodiments, the heating element includes a plurality heating elements as discrete heat spots or areas arranged in a radial manner about a circumference of the thermal conductivity probe. The discrete hot spots or areas can be circular, square, rectangular, oval, or other regular or irregular shape. The plurality of heating elements can be simultaneously or independently engaged to create different temperature gradients about a perimeter of the thermal conductivity probe 100. This configuration enables measuring differences in thermal conductivity of soil along a length or in a particular area.

The heating element is configured to increase temperature and generate heat in the surrounding soil and there are several methods employable to achieve heating through these elements. Resistance Heating: This method utilizes the resistance of a material to electric current flow, causing it to heat up. The most common type of resistance heating element is made of nichrome wire, an alloy that has high electrical resistance and can withstand high temperatures. Induction Heating: Induction heating employs electromagnetic induction to heat an electrically conductive material. An alternating current (AC) is passed through an induction coil, creating a magnetic field. When a conductive material is placed within this field, eddy currents are induced, generating heat within the material. Convection Heating: Convection heating involves the transfer of heat through a fluid medium, such as air or water. Infrared Heating: Infrared heating uses electromagnetic radiation in the infrared spectrum to transfer heat directly to objects or surfaces.

The thermal insulator is disposed about a circumference along a section length of the thermal conductivity probe 100. For instance, the thermal insulator can be a section of approximately 5 mm-400 mm (e.g., 100 mm) in length and 10-100 mm in diameter (e.g., 36 mm) with a wall thickness of approximately 1 mm-50 mm. Various different thermal insulator sizes and lengths can be provided to isolate thermistors, enabling measurements of thermal conductivity of soil or subsurface material across different distances using the heating element and thermistor. The use of various thermal insulator sizes enables measurements of local differences in thermal conductivity within a larger soil profile.

The thermal conductivity of the thermal conductivity probe 100 between the thermistor and the heating element should be as low as possible. This property ensures that changes in temperature detected by the thermistor are attributed to soil thermal conductivity and not due to thermal conductivity along a length of the thermal conductivity probe 100. Thus, the thermal insulator can be selected from many different types of material that are resistant to temperature. Polyimide (PI): Polyimide is a high-performance plastic known for its exceptional thermal stability and resistance to high temperatures. It can withstand continuous operating temperatures of up to 300° C. (572° F.) and short-term exposure to even higher temperatures. Polyetheretherketone (PEEK): PEEK is a high-performance thermoplastic with excellent mechanical properties and temperature resistance. It can withstand continuous operating temperatures of up to 250° C. (482° F.) and short-term exposure to even higher temperatures. Polyphenylene Sulfide (PPS): PPS is a rigid engineering plastic known for its high temperature resistance. It can withstand continuous operating temperatures of up to 240° C. (464° F.) and has good chemical resistance as well. Polyetherimide (PEI): PEI is a high-temperature thermoplastic known for its excellent mechanical and electrical properties. It can withstand continuous operating temperatures of up to 180-200° C. (356-392° F.) without significant degradation. PTFE, often known by the brand name Teflon, is a versatile plastic with exceptional temperature resistance. It can withstand continuous operating temperatures of up to 260° C. (500° F.) and is also known for its low friction and excellent chemical resistance.

The thermistor is disposed about a circumference along a section length of the thermal conductivity probe 100. For instance, the thermistor can be a section of approximately 5 mm-50 mm (e.g., 10 mm) in length and 10-100 mm in diameter (e.g., 36 mm) with a wall thickness of approximately 1 mm-50 mm. In one instance, the thermistor is defined by a wall section of thermal conductivity probe that includes thermally conductive material associated with one or more temperature sensors. In another instance, the thermistor is composed of one or a plurality of temperature sensors that are embedded in a sidewall about a circumference or along a length of the thermal conductivity probe. Thus, a discrete temperature level or temperature change in a region of soil around the thermal conductivity probe 100 is measurable.

There are several technologies that can be used for the thermistor. Thermocouples: Thermocouples are made of two different metals or metal alloys connected at one end to form a junction. When the junction is exposed to a temperature gradient, it generates a voltage proportional to the temperature difference. Resistance Temperature Detectors (RTDs): RTDs are temperature sensors that use the principle of electrical resistance. They consist of a pure metal or a metal alloy wire wound around a core. As the temperature changes, the resistance of the wire changes in a predictable manner. Semiconductor: semiconductor devices exhibit a large change in resistance with temperature. They are typically made of ceramic or polymer materials with a highly nonlinear resistance-temperature relationship. Infrared (IR) Sensors: IR sensors measure temperature based on the thermal radiation emitted by an object. They detect the intensity of infrared radiation emitted by the object and convert it into temperature readings. Integrated Circuit (IC) Temperature Sensors: IC temperature sensors are small electronic devices that contain a temperature-sensitive component integrated with signal processing circuitry. These sensors provide digital temperature output and are often used in applications where size, accuracy, and convenience are important. Bimetallic Strips: Bimetallic strips consist of two different metals bonded together with different coefficients of thermal expansion. As the temperature changes, the bimetallic strip bends due to the unequal expansion of the metals. This bending can be used to measure temperature changes.

In one embodiment, a plurality of thermistors 102 and 106 are provided, each separated from the at least one heating element 110 by a specified distance. Additionally, or alternatively, a plurality of thermistors 114 and 118 are provided, each separated from the at least one heating element 110 by a specified distance. In one particular embodiment, a plurality of thermistors 106 and 114 are provided, each separated from the at least one heating element 110 by a specified distance. In another embodiment, a plurality of two or more thermistors are provided on either side of the heating element 110, each separated from the at least one heating element 110 by a specified distance (e.g. 3-10 thermistors on either side of the heat element 110). The specified distance can be approximately 5 mm-400 mm (e.g., 100 mm) to sample temperature at different positions separated from the heating element 110.

Thermal conductivity is a measure of a material's ability to conduct heat. In the context of soil, thermal conductivity refers to the ability of soil to transfer heat. It is an important property in various fields, including agriculture, geophysics, and civil engineering, as it influences processes such as heat transfer, temperature distribution, and the design of geothermal systems. Soil is a heterogeneous and porous medium composed of solid particles, water, and air. The thermal conductivity of soil depends on several factors, including its composition, moisture content, density, and temperature. One or a plurality of thermistors 102 separated from the heating element 110 and insulated by one or more thermal insulators 108 enables measurements of the thermal conductivity. Here are some key points about thermal conductivity in soil. Composition: The type and proportion of soil constituents significantly affect its thermal conductivity. Different minerals have varying thermal conductivities, with metals being the best conductors and insulating materials having lower conductivities. Soils with higher proportions of conductive minerals, such as sands and silts, generally have higher thermal conductivities compared to organic-rich soils or clays. Moisture Content: Water has a higher thermal conductivity than air or dry soil particles. Therefore, as the moisture content in soil increases, its thermal conductivity also tends to increase. Saturated soils with high water content have higher thermal conductivities compared to dry or partially saturated soils. Density: Compacted or denser soils tend to have higher thermal conductivities than loose or less dense soils. When soil particles are tightly packed, there is greater contact between particles, allowing heat to transfer more efficiently. Temperature: Thermal conductivity in soil can vary with temperature. In general, the thermal conductivity of soils tends to increase with temperature due to changes in the physical properties of water and air. However, the effect may be more pronounced at lower temperatures and become relatively constant at higher temperatures. Anisotropy: Soil thermal conductivity can exhibit anisotropic behavior, meaning it can vary with direction. This is often observed in layered or structured soils where the arrangement of soil particles influences the directionality of heat flow.

In a further embodiment, a plurality of thermistors 106 and 114 flank the at least one heating element 110. For instance, thermistor 106 can be positioned above the heating element 110 and separated from the heating element 110 by the thermal insulator 108. The thermistor 114 can be positioned below the heating element 110 and separated from the heating element 110 by the thermal insulator 112. In certain embodiments, the thermistor 106 and the thermistor 114 are equidistant from the heating element 110. Alternatively, the thermistor 106 and 114 are differently spaced from the heating element 110. In some embodiments, a plurality of thermistors 102, 106, 114, and 118 flank the heating element 110. Optionally, a plurality of heating elements can be interspersed between and flanked by a plurality of thermistors, with different thermistors being configured to sample temperature dynamically for any given one of the plurality of heating elements 110. Thus, the flanking of the heating element 110 by thermistors 106 and 114 enables measurement of thermal conductivity of soil in different directions relative to the heating element 110. And, the optional inclusion of multiple heating elements and a plurality of interspersed thermistors enables measurement of thermal conductivity at one or more different depths along a column of the probe 100.

There can be differences in thermal conductivity with depth in soil and the flanking thermistors 106 interspersed with one or a plurality of heating elements 110 at different positions along a length of the probe 100 can enable more granular thermal conductivity of soil at different depths. These differences can arise due to several factors, including changes in soil composition, moisture content, and density. Soil Composition: The composition of soil can vary with depth. Different layers may have different proportions of minerals, organic matter, and moisture. Since different materials have varying thermal conductivities, the thermal conductivity of soil can change deeper into the soil profile. Moisture Content: Moisture content in soil often decreases with depth, especially in dry regions or well-drained soils. The presence of water in soil increases its thermal conductivity. So, if moisture content decreases with depth, the thermal conductivity of the soil may also decrease accordingly. Density and Compaction: Soil density and compaction can also vary with depth. Compacted or denser layers tend to have higher thermal conductivities compared to loose or less dense layers. Therefore, if there are variations in density or compaction deeper into the soil, it can result in differences in thermal conductivity. Geological and Environmental Factors: Geological factors, such as the presence of rock formations, bedrock, or soil horizons, can introduce variations in thermal conductivity with depth. Additionally, environmental factors like temperature gradients, groundwater movement, and soil disturbances can influence the distribution of thermal conductivity in the subsurface. Thus, conducting site-specific studies and measurements can provide a more accurate understanding of the thermal conductivity profile in a particular location. Profiling the thermal conductivity with depth is crucial for applications like geothermal energy systems, underground construction, and studying heat transfer in the subsurface. These profiles help in determining the thermal properties of different soil layers, understanding heat flow patterns, and optimizing the design and performance of related systems. Thus, various quantities of the thermistors can be provided with up to ten or more on one or both sides of the heating element 110, separated by thermal insulators, to enable measurements of temperature at different distances from the heating element 110. Additionally, multiple heating elements can be provided along the length of the thermal conductivity probe 110, to enable sampling of thermal conductivity properties at different depths. The multiple heating elements can be dispersed or flanked by one or more combinations of thermistors and thermal insulators, with each of the thermistors being independently available for temperature measurements for any given heating element.

In a further embodiment, the at least one heating element 110 is disposed between an upper thermal insulation section 108 and lower thermal insulation section 112. The heating element 110 can be a section of approximately 5 mm-100 mm (e.g., 45 mm) in length and 10-100 mm in diameter (e.g., 36 mm) with a wall thickness of approximately 1 mm-50 mm. The upper thermal insulation section 108 and/or the lower thermal insulation section 112 can be approximately 5 mm-400 mm (e.g., 100 mm) in length and 10-100 mm in diameter (e.g., 36 mm) with a wall thickness of approximately 1 mm-50 mm. The heating element 110 can be a solid disk segment of the probe 100, or can be constructed as a hollow ring or surface band along a portion of the probe 100, or can be composed of one or more discrete bands or areas on a surface of the probe 100. The thermal insulation section 108 and/or 112 can be a solid disk segment of the probe 110, or can be constructed as a ring or surface band along a portion of the probe 100. Additionally, the thermal insulation section 108 and/or 112 can be formed from a composite or layered set of disparate materials with different properties. The thermal insulation section 108 and/or 112 can each possess different thermal insulation properties, or can provide the same thermal insulation properties. The thermal insulation section 108 and/or 112 can be removable and/or replaceable such as via threads or snap locks with the probe 100, thus enabling different degrees, lengths, and distances of thermal insulation to be used, swapped, and removed for any given soil profile.

To vary the thermal insulation degree of materials, several factors can be considered and modified. Here are some key considerations and techniques. Material Selection: Different types of plastics have varying thermal insulation properties. Materials with lower thermal conductivity provide better insulation. Polymers like expanded polystyrene (EPS), polyurethane (PUR), and polyisocyanurate (PIR) are commonly used for thermal insulation due to their low thermal conductivity. Foaming or Blowing Agents: Introducing foaming or blowing agents into plastic materials can increase their insulation properties. These agents create small air pockets within the plastic, which reduce heat transfer through conduction and convection. Foamed plastics, such as foam boards, are widely used for thermal insulation purposes. Thickness: Increasing the thickness of plastic insulation can improve its thermal resistance and insulation capabilities. Thicker layers of insulation create a larger barrier to heat transfer. Reflective Coatings: Applying reflective coatings or films to the surface of plastic materials can enhance their thermal insulation performance. These coatings reflect radiant heat, reducing the amount of heat absorbed by the plastic and improving its insulation properties. Multi-Layer Construction: Using multiple layers of plastic materials with different thermal properties can enhance thermal insulation. For example, constructing a plastic composite with alternating layers of high-density and low-density plastics can create an effective barrier against heat transfer. Cellular Structure: Cellular plastics, such as those with closed-cell structures, offer improved thermal insulation properties. The closed-cell structure traps air within the plastic, reducing heat conduction. Encapsulation: Enclosing plastic insulation within a protective barrier can help maintain its thermal properties over time. This can involve using coatings, films, or protective layers to shield the insulation from moisture, physical damage, and degradation, which could impact its insulation performance.

In various embodiments, at least one upper thermistor set is composed of an upper first thermistor section 102 and an upper second thermistor section 106, the upper first thermistor section 102 and the upper second thermistor section 106 being thermally isolated from each other by an upper thermistor thermal insulation section 104 and being thermally isolated from the at least one heating element 110 by a lower thermal insulation section 108. Alternatively, or additionally, at least one lower thermistor set is composed of a lower first thermistor section 118 and a lower second thermistor section 114, the lower first thermistor section 118 and the lower second thermistor section 114 being thermally isolated from each other by a lower thermistor thermal insulation section 116 and being thermally isolated from the at least one heating element 110 by an upper thermal insulation section 112. The upper thermistor set or the lower thermistor set can be inserted at various positions along a length of the probe 100, using screw, snap, or other similar fastening means. Spacers can be used to position the upper thermistor set or the lower thermistor set as needed or desired along a length of the probe 100. Additionally, either or both the upper thermistor set or the lower thermistor set can be combined to create composite thermistor sets stacked, with or without spacers or intervening heating elements 110, along a length of the probe 100.

In a further embodiment, probe 100 further includes a cone penetration head 120, including one or more of the following sensors: pore pressure, friction, depth, and inclination. The cone penetration head (CPT) 120 can be attached and/or removed to and/or from the probe 100 using threads, snaps, fasteners, or other similar mechanisms. Thus, the CPT 120 can removably attach to at least one heating element 110; at least one thermal insulator 108; at least one thermistor 106 thermally isolated from the at least one heating element 110 by the at least one thermal insulator 108 using a threaded member 128. Various types or configurations of CPT 120 can be employed such that the probe 100 enables a combination of CPT sensor capabilities in association with thermal conductivity sensor capabilities, to yield enhanced soil and subsurface profile analysis.

Cone Penetration Testing (CPT) is a widely used in-situ geotechnical testing method that provides valuable information about the subsurface soil or sediment layers. It involves pushing a cone-shaped penetrometer into the ground at a constant rate and measuring the resistance and other parameters as the cone advances. The CPT equipment 120 consists of a steel cone 126, typically made of hardened steel that is pushed into the ground using hydraulic or mechanical equipment, and data is continuously recorded during the penetration process. The cone 126 typically has a friction sleeve 122 to measure the frictional resistance along the cone shaft. The CPT 120 may include a pore pressure element 124 and/or one or more other types of sensors to measure the following data. Cone Tip Resistance: This measurement represents the resistance encountered by the cone as it penetrates the soil. It provides an indication of the soil's strength or stiffness. 2. Sleeve Friction: This measurement represents the frictional resistance along the cone shaft. It provides information about the shear strength and the relative density of the soil. Pore Water Pressure (u): In some CPT systems, a pore pressure sensor is included to measure the excess pore water pressure generated during the test. This measurement is useful in assessing soil consolidation characteristics and estimating soil permeability. CPT 120 can also include additional measurements or variations, such as the use of electrical conductivity sensors to identify soil contamination, piezocone testing to measure hydraulic conductivity, or seismic cone testing to evaluate soil stiffness and seismic properties. The data obtained from CPT 120 is typically recorded in real-time and is used to create a profile of the subsurface soil layers. This information is valuable to assess soil properties, such as shear strength, stiffness, soil type, layer thicknesses, and stratigraphy. The data can be further analyzed to estimate parameters like soil bearing capacity, settlement potential, liquefaction potential, and slope stability.

FIG. 2 is an environmental view of a thermal conductivity probe, in accordance with an embodiment of the invention. In one embodiment, site 200 includes a subsurface 202 in which a thermal conductivity probe 100 is pushed. The thermal conductivity probe 100 includes, but is not limited to, at least one heating element 110; at least one thermal insulator 108; at least one thermistor 106 thermally isolated from the at least one heating element 110 by the at least one thermal insulator 108. The subsurface 202 includes a seafloor, terrestrial, or extraterrestrial surface. In certain embodiments, the probe 100 further includes one or more of thermistor 102, thermal insulator 104, thermal insulator 112, thermistor 114, thermal insulator 116, thermistor 118, and/or CPT 120.

The probe 100 is depicted inserted or disposed within the subsurface 202. Heating element 110 is used to increase temperature locally in the subsurface 202. The thermal insulator 108 substantially prevents the heating element 110 from directly affecting the thermistor 106. Thus, the increase in local temperature induced by the heating element 110 permeates and travels in the subsurface 202. The thermistor 106 senses the increased temperature in the subsurface 202, the extent of which is dependent upon the thermal conductivity in the subsurface 202.

The probe 100 can be inserted into the subsurface 202 using various techniques. Direct Push Method: This method involves using a hydraulic or mechanical push system to insert the probe 100 directly into the subsurface. The probe 100 is pushed into the ground using force, typically applied by a hydraulic ram or a static weight system. This method is suitable for cohesive and granular soils and can provide real-time measurements during penetration or after the probe 100 has reached a desired depth or location. Hammering Method: In this technique, the probe 100 is driven into the subsurface using a hammering action. The hammer can be manual or powered by a mechanical device. This method is often used for dense or compacted soils and may require pre-drilling or pre-auguring to facilitate penetration. Vibratory Method: Vibratory techniques involve using a vibratory driver or a vibrator attached to the probe 100. The vibrations help reduce the subsurface resistance, making it easier for the probe 100 to penetrate the subsurface. This method is useful for cohesive soils and can improve penetration efficiency. Drilling Method: In some cases, a drilling rig may be used to create a borehole or pilot hole before inserting the probe 100. Once the hole is drilled, the probe 100 is lowered into the borehole using appropriate equipment. This method is suitable for more challenging subsurface conditions, such as hard or rocky soils. Jetting Method: The jetting method involves using water or air pressure to fluidize the soil around the probe 100, reducing friction and facilitating penetration. Water or air jets are directed near the tip of the probe 100, allowing it to advance into the ground. This method is effective in loose or soft soils but may not be suitable for cohesive or compacted soils.

In various embodiments, the probe 100 can be used in various subsurface types encountered in geotechnical and geological investigations, including any of the following examples. Sand: Sand is composed of granular particles ranging in size from 0.06 mm to 2 mm. It is often loose and provides good drainage properties. Clay: Clay consists of fine particles with a size less than 0.002 mm. It has cohesive properties, retains water well, and can be prone to shrinkage and swelling. Silt: Silt particles are finer than sand but coarser than clay, with sizes ranging from 0.002 mm to 0.06 mm. Silt has intermediate properties between sand and clay. Gravel: Gravel consists of larger particles, usually ranging from 2 mm to 60 mm in size. It is coarser than sand and provides good load-bearing capacity. Loam: Loam is a mixture of sand, silt, and clay in roughly equal proportions. It offers good drainage while retaining moisture. Peat: Peat is formed from partially decomposed organic matter and is typically found in marshy or wetland areas. It has a high moisture content and low strength. Rock: The subsurface can contain various types of rocks, including sedimentary, igneous, and metamorphic rocks. Examples include limestone, granite, shale, sandstone, basalt, and marble, each with its own distinct properties. Fill Materials: In some cases, the subsurface may contain fill materials, which are man-made deposits often used to raise ground levels or support construction activities. Fill materials can consist of various materials such as sand, gravel, crushed stone, or even construction waste.

The subsurface 202 can further include fresh or saltwater subsurfaces, which can include sediments. The ocean floor is covered with a layer of sediments, which are a mixture of various materials that have settled over time. Terrigenous Sediments: These sediments originate from land and are transported to the ocean by rivers, wind, and other processes. Terrigenous sediments can include clay, silt, sand, and gravel, depending on the proximity to coastlines and the geological makeup of the surrounding land. Biogenic Sediments: Biogenic sediments are composed of the remains of marine organisms, such as shells, skeletons, and microorganisms. For example, calcium carbonate shells from marine organisms like foraminifera, coccolithophores, and corals can accumulate on the seafloor and form calcareous ooze. Volcanic Ash and Hydrothermal Deposits: In regions with active volcanism or hydrothermal activity, volcanic ash and minerals from hydrothermal vents can contribute to the ocean floor's composition.

The locations of the subsurface 202 and the places for which the probe 100 is usable can include various seafloor surfaces, such as any one or more of the following examples. Abyssal Plains: These are relatively flat areas on the ocean floor covered by fine-grained sediments. Mid-Ocean Ridges: Mid-ocean ridges are underwater mountain ranges where tectonic plates are spreading apart, resulting in volcanic activity and the formation of new crust. Seamounts and Guyots: Seamounts are underwater mountains that rise above the seafloor, whereas guyots are flat-topped seamounts that have eroded over time. Trenches: Trenches are deep, elongated depressions in the ocean floor associated with subduction zones where one tectonic plate is forced beneath another. Hydrothermal Vents: Hydrothermal vents are areas where hot, mineral-rich fluids are released from the seafloor, supporting unique ecosystems and depositing minerals.

The probe 100 is therefore usable to measure the thermal conductivity of the subsurface 202 through operations including at least (i) inserting the probe 100 to a location or depth for analysis such that the probe is in contact with the subsurface 202; (ii) activating the heating element 110 to transfer heat into the subsurface 202; (iii) record the temperature at one or more times or intervals using the thermistor 106 with sufficient time for the heat to propagate through the subsurface 202; (iv) analyze the data after collecting temperature readings over a suitable duration to observe how the temperature changes over time in the subsurface 202; (v) and calculate thermal conductivity using a model or equation that factors in temperature change, time, and/or distance of the thermistor 106 from the heating element 110.

Many models are usable to convert temperature to thermal conductivity. One model for determining thermal conductivity using temperature change over time is the one-dimensional heat conduction equation. The one-dimensional heat conduction equation is expressed as:

$$k = -q * (dx/dT)$$

where: q is the heat flux (amount of heat transferred per unit area per unit time), k is the thermal conductivity of the soil, dT/dx is the temperature gradient (rate of change of temperature with respect to distance). This particular equation can be used to determine thermal conductivity by performing operations including (i) apply a constant heat flux (q) to the soil sample; (ii) measure the temperature change (dT) at a specific distance (x) from the heat source over a certain period of time, recording the temperature readings at regular intervals; (iii) calculate the distance change (dx) based on the position of the temperature sensor; and (iv) substitute the measured values of q, dx, and dT into the equation to obtain the thermal conductivity of the soil. This example model assumes steady-state conditions, meaning that the temperature distribution in the soil sample has reached a stable state. Additionally, this model assumes one-dimensional heat transfer, which might not accurately represent all subsurface types and conditions. There are other 2D and 3D models that can be used, including for example:

$$q = -k * (d^2 T/dx^2 + d^2 T/dy^2)$$

where q is the heat flux, k is the thermal conductivity, T is the temperature, and $d^2 T/dx^2$ and $d^2 T/dy^2$ are the second partial derivatives of temperature with respect to x and y, respectively. An additional example models includes, for example:

$$q = -k * (d^2 T/dx^2 + d^2 T/dy^2 + d^2 T/dz^2)$$

where q is the heat flux, k is the thermal conductivity, T is the temperature, and $d^2 T/dx^2$, $d^2 T/dy^2$, and $d^2 T/dz^2$ are the second partial derivatives of temperature with respect to x, y, and z, respectively.

In certain embodiments, the probe 100 can be used with the CPT 120 head to collect and/or correlate various CPT data with thermal conductivity data for a given location in the subsurface 202. This data can be stored together in association with a 3D positional GPS location to establish 3D model of thermal conductivity and/or CPT data for an area and/or depth of a subsurface 202. Various cone penetration testing (CPT) of the subsurface 202, such as the seafloor, can provide valuable data about the subsurface conditions and geotechnical properties. Here are some of the key data that can be gathered with cone penetration in the seafloor. Cone Resistance (qc): The cone resistance is a measure of the resistance encountered by the cone penetration probe as it advances into the soil. It provides an indication of the soil's strength and stiffness. The cone resistance is measured in terms of cone tip resistance (qc) and can be used to estimate soil properties such as undrained shear strength and relative density. Friction Sleeve Resistance (fs): The friction sleeve is located behind the cone tip and measures the frictional resistance between the sleeve and the surrounding soil. It provides information about the skin friction or adhesion of the soil, which is useful in cohesive soils. Pore Water Pressure (u): Cone penetration tests can measure the pore water pressure in the seafloor. Pore water pressure is useful for assessing soil behavior, stability, and the potential for liquefaction. Sleeve Friction Ratio (Rf): The sleeve friction ratio is calculated by dividing the friction sleeve resistance (fs) by the cone tip resistance (qc). It provides an indication of the relative proportion of frictional resistance to total resistance and can help characterize soil types. Seabed Layering: By continuously measuring the cone resistance and friction sleeve resistance as the probe advances, CPT can identify distinct layers or changes in the seafloor sediment composition and stratigraphy. Soil Classification: Based on the measured cone resistance and friction sleeve resistance, along with other parameters, soil types can be classified using established soil classification systems (e.g., the Unified Soil Classification System or the International Soil Classification System). Soil Strength and Shear Parameters: CPT data can be used to estimate geotechnical properties such as undrained shear strength, effective stress parameters, and soil stiffness, which are crucial for geotechnical design and analysis. Groundwater Conditions: The measured pore water pressure during cone penetration can provide insights into the groundwater conditions, including the presence of artesian conditions, hydraulic gradients, and potential water flow patterns. These data points gathered through cone penetration in the seafloor are valuable for geotechnical investigations, foundation design, offshore engineering, sediment characterization, seafloor electrical and conduit engineering, and site assessment in marine environments.

Figure 3:
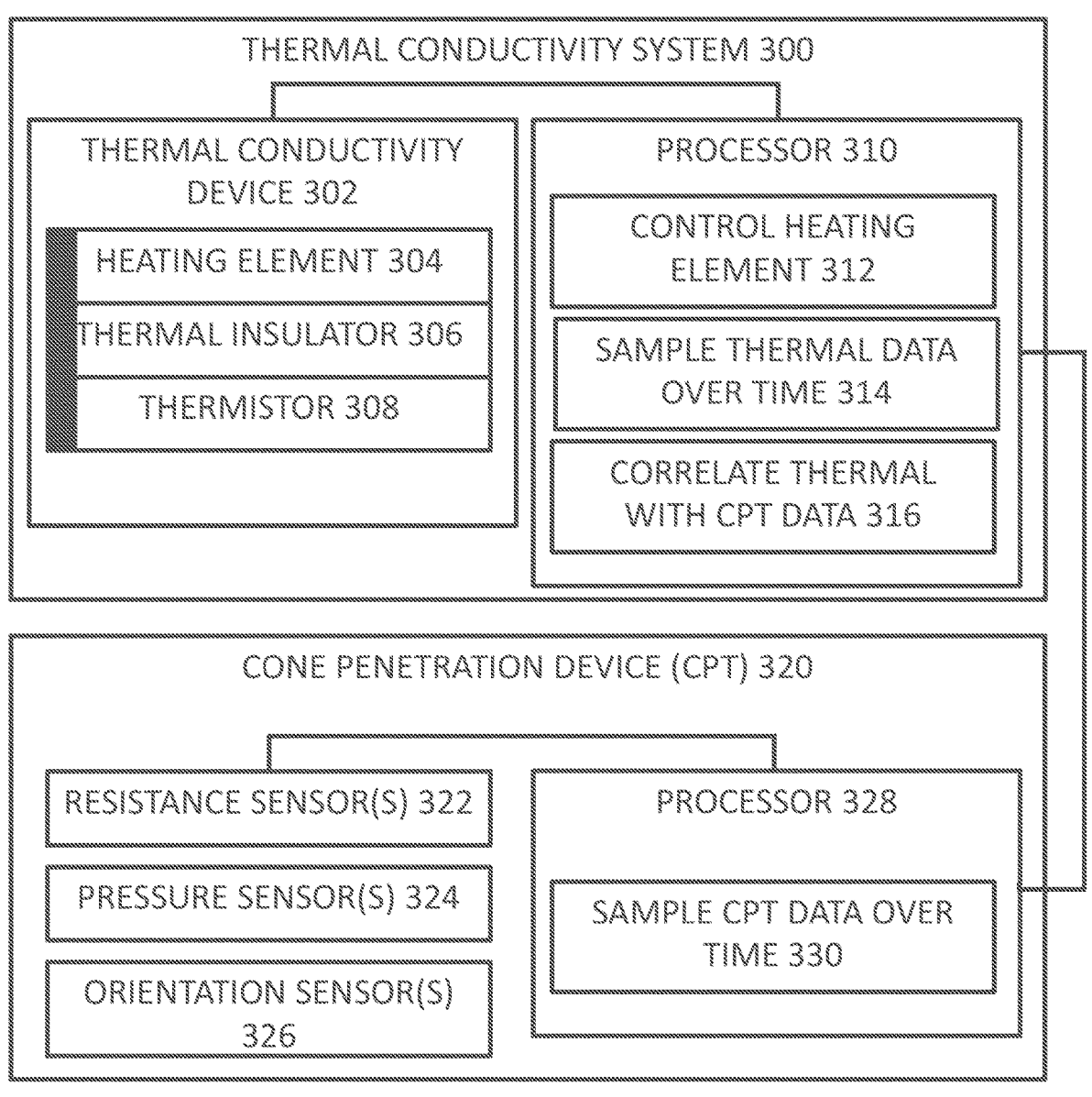
FIG. 3 is a system diagram of a thermal conductivity and CPT system, in accordance with an embodiment of the invention.

FIG. 3 is a system diagram of a thermal conductivity and CPT system, in accordance with an embodiment of the invention. In one embodiment, thermal conductivity system 300 includes, but is not limited to, thermal conductivity device 302 with heating element 304, thermal insulator 306, and thermistor 308; and processor 310 configured to perform operations of control heating element 312, sample thermal data over time 314, and correlate thermal with CPT data at 316. Optionally, the thermal conductivity system 300 can further include a cone penetration device 320 with resistance sensor 322, pressure sensor 324, orientation sensor 326, and processor 328 configured to sample CPT data over time 330.

The thermal conductivity system 300 can include an integrated probe with the thermal conductivity device 30-2 and the processor 310. Alternatively, the thermal conductivity system 300 can be decentralized with one or more thermal conductivity devices 302 in communication with one or more processors 310. For example, the thermal conductivity system 300 can include probe 100 with an integrated processor 310. Alternatively, the thermal conductivity system 300 can include a plurality of probes 100 each in wired or wireless communication with one or more processors 310. The cone penetration device 320 can similarly be integrated with the thermal conductivity system 300 or can be partially or entirely decentralized with wired or wireless communication therebetween. In one particular embodiment, the thermal conductivity system 300 and the cone penetration device 320 are unified into a probe with wired data communication to one or more processors 310 or 328 for performing operations associated therewith.

The thermal conductivity device 302 includes a set of heating element 304, thermal insulator 306, and thermistor 308. The device 302 can include multiple sets of heating element 304, thermal insulator 306, and thermistor 308. Alternatively, the device 302 can include a set with a plurality of any of heating element 304, thermal insulator 306, and thermistor 308. For instance, the device 302 can include two or more heating elements 304, each separated from two or more thermistors 308, by two or more thermal insulators 306. In one particular embodiment, one heating element 304 is flanked by four thermistors 308, each separated from the heating element 304 and other thermistors 308 by thermal insulator 306. Alternatively, the system 300 can include two or more thermal conductivity devices 302 positioned along a length of one probe 100. Furthermore, the system 300 can include a plurality of thermal conductivity devices 302 distributed across multiple probes 100. Many combinations of devices 302 are possible, each with different combinations or instances of heating element 304, thermal insulator 306, and thermistor 308.

The processor 310 can be physically integrated into the thermal conductivity system 300 or can be wired or wirelessly linked to the thermal conductivity system 300 or thermal conductivity device 302. Various processor types or technologies are usable, including for example any of the following. Intel Core Processors: Intel Core processors are widely used in personal computers and laptops. They come in various generations, such as the Intel Core i3, i5, i7, and i9 series. Each generation offers improved performance and features compared to its predecessor. AMD Ryzen Processors: AMD Ryzen processors are a popular alternative to Intel's offerings. They provide high-performance computing power and are known for their multitasking capabilities and affordability. Ryzen processors are commonly used in gaming PCs, workstations, and laptops. Qualcomm Snapdragon Processors: Qualcomm Snapdragon processors are primarily designed for mobile devices, including smartphones and tablets. They offer efficient power consumption, integrated graphics, and cellular connectivity features. Snapdragon processors are known for their performance in the Android ecosystem. Apple M1 Chip: The Apple M1 chip is a custom-designed processor developed by Apple for its Mac computers. It utilizes ARM architecture and offers high performance, energy efficiency, and improved battery life. The M1 chip integrates multiple components, including the CPU, GPU, and Neural Engine, for enhanced performance and power optimization. IBM Power Processors: IBM Power processors are used in high-performance computing systems, servers, and enterprise-grade hardware. They are known for their scalability, reliability, and robust performance in demanding computing environments.

The processor 310 can be communicatively linked with the thermal conductivity device 302 to receive and/or transmit data or control instructions. Wired communication can be accomplished using printed circuit board traces or a wired conductor. Wireless communication can be accomplished using any one or more of the following examples: Wi-Fi (Wireless Fidelity): Wi-Fi is a widely used wireless communication method that allows devices to connect to a local area network (LAN) or the internet wirelessly. Wi-Fi operates based on the IEEE 802.11 standard and uses radio waves to transmit data between devices within a limited range. Bluetooth: Bluetooth is a short-range wireless communication technology used for data transfer between devices in close proximity. Bluetooth operates in the unlicensed 2.4 GHz frequency band and enables wireless connectivity between devices. Cellular Networks: Cellular networks provide wireless data communication over a wide area, typically using cellular towers and base stations. Cellular networks, such as 3G, 4G LTE, and 5G, enable mobile devices to connect to the internet and other networks wirelessly. Cellular networks offer higher data transfer speeds and wider coverage compared to Wi-Fi or Bluetooth. NFC (Near Field Communication): NFC is a short-range wireless communication technology that enables data transfer between devices in close proximity (within a few centimeters). Zigbee: Zigbee is a wireless communication standard based on the IEEE 802.15.4 standard. Zigbee operates in the 2.4 GHz frequency band and allows devices to form ad-hoc networks or mesh networks for data transmission. RFID (Radio Frequency Identification): RFID technology uses radio waves to identify and track objects wirelessly. RFID tags or transponders are attached to objects, and when they come into range of an RFID reader, data is exchanged between the tag and the reader.

The cone penetration device 320 is an optional component to the thermal conductivity system 300. When present, the cone penetration device 320 can be physically incorporated with the thermal conductivity system, or can be wired or wirelessly linked therewith. For instance, the CPT 320 can be integrated into the probe 100 with the thermal conductivity system 300. Alternatively, the CPT 320 can be part of one probe that is separate from and/or useable with another probe that includes the thermal conductivity system 300. In certain embodiments, a plurality of probes are provided in a system that includes some with the thermal conductivity system 300 and some with CPT 320. In certain embodiments, the processor 310 and the processor 328 are combined into a single processor. Within the CPT 320, the resistance sensor 322, pressure sensor 324, and/or orientation sensor 326 are optionally included.

In cone penetration testing (CPT), resistance sensors are used to measure the cone resistance (qc) and friction sleeve resistance (fs) as the cone penetration probe advances into the soil. These sensors provide valuable data about the geotechnical properties of the subsurface. The resistance sensors work based on the principle of measuring the force or pressure exerted by the soil on the cone or friction sleeve. Cone Resistance (qc) Sensor: The cone resistance sensor is located at the tip of the cone penetration probe. As the probe is pushed into the soil, the cone encounters resistance from the surrounding soil. This resistance is transferred to the cone resistance sensor, which typically consists of a load cell or pressure transducer. The load cell or transducer converts the applied force or pressure into an electrical signal. The electrical signal is then amplified, conditioned, and processed by the data acquisition system connected to the cone penetration equipment. The processed signal is recorded and used to determine the cone resistance (qc) value, which represents the strength and stiffness of the soil. Friction Sleeve Resistance (fs) Sensor: The friction sleeve resistance sensor is located behind the cone tip and measures the frictional resistance between the friction sleeve and the soil as the probe advances. The friction sleeve typically consists of a cylindrical metal sleeve with pressure-sensitive devices, such as strain gauges or pressure transducers, embedded within it. As the friction sleeve encounters frictional forces from the soil, these forces are transferred to the embedded sensors, which measure the applied pressure or strain. Similar to the cone resistance sensor, the electrical signals from the sensors are amplified, conditioned, and processed by the data acquisition system. The processed signals are used to determine the friction sleeve resistance (fs), which provides information about the skin friction or adhesion of the soil. The cone resistance (qc) and friction sleeve resistance (fs) data obtained from the sensors are typically recorded continuously during the cone penetration test. These resistance measurements, along with other parameters such as pore water pressure and cone penetration rate, are analyzed to evaluate soil properties, assess subsurface conditions, and aid in geotechnical engineering and site characterization.

Inclination sensors, also known as inclinometers or tilt sensors, can be used in cone penetration testing (CPT) to measure the inclination or tilt of the cone penetration probe during the test. These sensors provide information about the verticality or angle of the probe, which is useful for analyzing the geometry and alignment of the test and interpreting the CPT data accurately. Sensor Placement: Inclination sensors are typically installed on the cone penetration probe itself, usually near the tip or in the vicinity of the cone. The sensors may be integrated into the probe assembly or attached externally, depending on the specific design of the CPT equipment. Measurement Principle: Inclination sensors use various technologies to measure the tilt angle of the probe. Commonly used technologies include accelerometers, gyroscopes, or a combination of both. These sensors detect changes in the orientation of the probe with respect to gravity and provide corresponding electrical signals. Data Acquisition: The electrical signals from the inclination sensors are acquired by a data acquisition system connected to the CPT equipment. The signals are typically analog or digital and represent the tilt angle or inclination of the probe in real-time. Data Processing and Analysis: The acquired tilt angle data is processed and recorded by the data acquisition system. The data can be visualized and analyzed to assess the verticality and alignment of the probe during the test. Deviations from the vertical alignment can indicate potential issues with the test, such as bent rods or uneven ground conditions. Correction and Interpretation: The inclination data obtained from the sensors can be used to correct and interpret other CPT measurements. For example, correcting the cone resistance (qc) and friction sleeve resistance (fs) values based on the inclination data can provide more accurate representations of the soil properties and geotechnical parameters. Quality Control: Inclination sensors play a crucial role in quality control during CPT. Monitoring the probe inclination helps ensure that the test is performed properly and that the acquired data is reliable and representative of the subsurface conditions.

Figure 4:
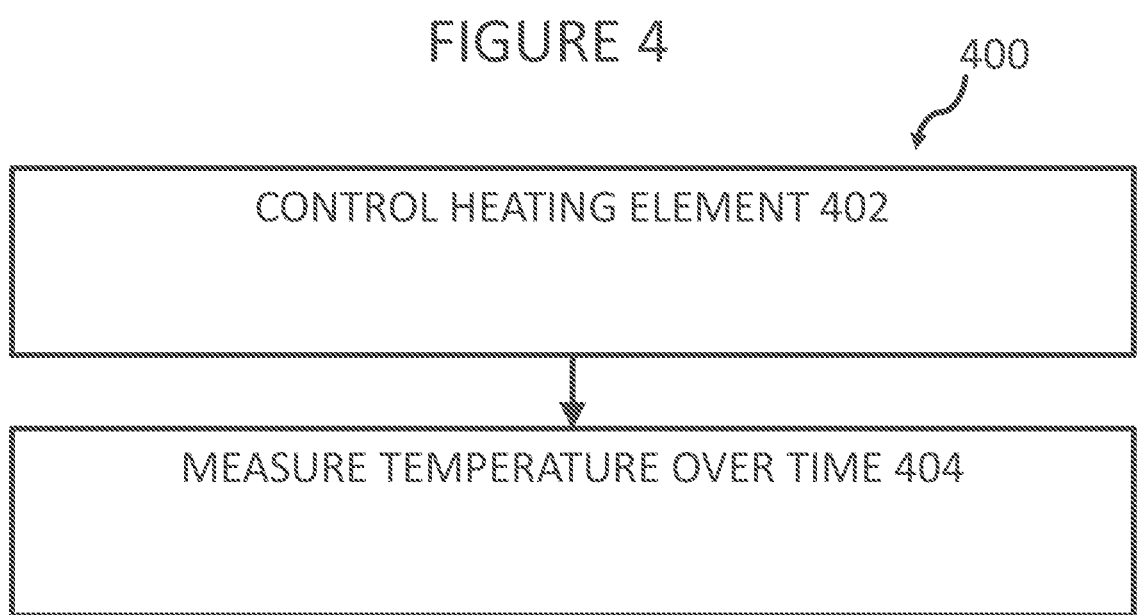
FIG. 4 is a flow diagram of a computer process for operating a thermal conductivity probe, in accordance with an embodiment of the invention.

FIG. 4 is a flow diagram of a computer process 400 for operating a thermal conductivity probe, in accordance with an embodiment of the invention. In one embodiment, a computer processor is configured to perform operations including at least controlling the at least one heating element at 402 and measuring temperature using the at least one thermistor over time at 404.

In certain embodiments, the computer process 400 is implemented on a central processing unit (CPU), such as the following. 1. x86 Architecture: The x86 architecture includes various generations and families of processors, such as Intel Core i7, i5, and i3 series, as well as AMD Ryzen processors. These processors are designed for general-purpose computing and are commonly used in desktops, laptops, and servers. 2. ARM Architecture: ARM (Advanced RISC Machines) processors are known for their energy efficiency and are designed using a Reduced Instruction Set Computing (RISC) architecture. Companies like Qualcomm, Apple, and Samsung utilize ARM-based processors in their smartphones, tablets, and other portable devices. ARM processors are usable for their power efficiency. 3. Power Architecture: The Power Architecture, previously known as PowerPC, is known for its scalability, reliability, and performance in enterprise environments. They are commonly found in IBM's Power Systems servers and certain gaming consoles like the Xbox 360 and PlayStation 3 (previous-generation consoles). 4. RISC-V Architecture: RISC-V is an open-source instruction set architecture (ISA) that is suitable for various applications. RISC-V processors have the advantage of being open and flexible, allowing companies and individuals to design their own processors based on the RISC-V instruction set. 5. Other Architectures: In addition to the above-mentioned architectures, there are several other specialized processors used in specific domains. For example, IBM's z/Architecture is designed for mainframe computers, Intel's Itanium architecture targeted high-performance computing (HPC) applications, and NVIDIA's GPUs (Graphics Processing Units) are used extensively for parallel computing and graphics-intensive tasks like gaming and artificial intelligence.

The computer process 400 can be implemented using one or more computer programming languages that are compiled to configure the CPU, such as the following. Python: Python is a versatile language usable in web development, scientific computing, data analysis, artificial intelligence, and automation. 2. JavaScript: JavaScript is the language of the web and is primarily used for front-end web development. It is usable to create interactive web pages and dynamic user interfaces. 3. Java: Java is a general-purpose programming language known for its platform independence and can be used to develop a wide range of applications, including desktop software, mobile apps (Android), enterprise systems, and large-scale web applications. 4. C++: C++ is a powerful, high-performance language useable for system programming and resource-intensive applications. 5. C #: C # is a modern, object-oriented language usable in Windows development, including desktop applications and web services. 6. Swift: Swift is a programming language developed by Apple for iOS, macOS, watchOS development. 7. Kotlin: Kotlin is a statically-typed programming language that runs on the Java Virtual Machine (JVM). It is useable for Android app development 8. Ruby: Ruby is useable for web development (Ruby on Rails framework). 9. Go: Go (or Golang) is a statically-typed language that is suitable for network programming and distributed systems. 10. Rust: Rust is a systems programming language that is usable in areas like systems programming and web browsers.

In some embodiments, a computer processor such as processor 310 is configured by a computer program to execute and control the at least one heating element at 402. For instance, the heating element can include the heating element 110 of the probe 100. The control of the at least one heating element 402 can include increasing a temperature, decreasing a temperature, turning on, turning off, or pulsing the heating element on/off. In cases of turning on the heating element, the computer processor can apply steady current for a constant temperature or can increase the temperature linearly or exponentially. In cases of turning off the heating element, the computer processor can turn off current or can decrease the temperature linearly or exponentially. In cases of pulsing the heating element on/off, the computer processor can turn on/off the heating element at regular or irregular intervals, such as intervals that increase or decrease over time. Additionally, the computer processor can turn on/off the heating element over time with steady temperature or with increasing or decreasing temperature. In certain embodiments, the computer processor can control the heating element based on user instructions, such as for temperature, duration, or rise/sink profiles. In other embodiments, the computer processor can control the heating element automatically based on programmed instructions or based in part using sensor inputs. For instance, the computer processor can detect a depth, lack of movement, time, or soil factor and then automatically control the heating element. Also, the computer processor can adjust the control of the heating element using input of the thermistor. For example, in cases where the thermistor rises too quickly or does not respond, the computer processor can adjust the control of the heating element to increase or decrease temperature as needed.

In some embodiments, a computer processor such as processor 310 is configured by a computer program to execute and measure temperature using the at least one thermistor over time at 404. For instance, the thermistor can include the thermistor 102 of the probe 100.

The computer processor can measure temperature at various times relative to the control of the heating element, including before, during, or after increasing the temperature of the heating element. Additionally, the computer processor can measure temperature at regular or irregular intervals relative to the control of the heating element. For instance, the computer processor can measure temperature every specified number of seconds after the heating element has been energized. The interval of the temperature measurement can increase or decrease over time. For example, the temperature measurement interval can initially be a first number of seconds, but then be adjusted to a more frequent interval of a second number of seconds at such time that an initial temperature rise is detected. Thereafter, in certain embodiments, the temperature interval can then be adjusted to a less frequent interval of a third number of seconds after the temperature reaches a steady state or begins to decrease. In other embodiments, the temperature interval is measured in near real-time continuously during control of the heating element. The computer processor can also measure temperature at times when the heating element is not in use, such as for the purpose of sampling temperatures at various subsurface depths during probe insertion. A plurality of thermistors at different positions are employable by the computer processor to measure temperature at various locations or distances from the heating element 110 at the same or different times. These operations are usable to detect and measure differences in soil thermal conductivity is different directions relative to the heating element.

In one particular embodiment, the computer processor can be used to control the heating element and measure the temperature using a thermistor over time using the following steps. 1. Select the thermistor: Choose a suitable thermistor that is sensitive to temperature changes within a select range for measurement. 2. Prepare the thermistor: Connect the thermistor to a suitable measurement circuit or device. This typically involves connecting the thermistor to a voltage divider circuit or a Wheatstone bridge circuit to convert its resistance changes into measurable voltage or current changes. 3. Install the thermistor and heating element in the soil: Place the probe into the soil at the desired depth or position to measure the thermal conductivity. 4. Calibrate the system: Before conducting long-term measurements, it's possible to calibrate the system, including comparing the resistance or voltage output of the thermistor at known temperatures. You can use a precision thermometer or a temperature-controlled chamber to establish calibration. 5. Measure temperature changes: Connect the measurement circuit to a data acquisition system capable of logging the thermistor's resistance or voltage output over time. Set up the data acquisition system to measure and record data at regular intervals. 6. Monitor soil conditions: In addition to measuring temperature changes, it's possible to use the CPT element, such as CPT 120 to monitor other relevant parameters or even soil moisture content, ambient temperature, and humidity. These factors can affect the thermal conductivity of the soil and can be recorded simultaneously. 7. Calculate thermal conductivity: To determine the thermal conductivity of the soil, the computer processor can employ appropriate mathematical models or equations, such as the one-dimensional heat conduction equation.

In one particular embodiment, the computer processor is configured to perform operations including at least: energize the at least one heating element to emit heat; measure temperature using the at least one thermistor to detect a preset temperature gain above ambient; de-energize the at least one heating element to stop emitting heat; and measure temperature using the at least one thermistor over time to determine a decay profile. The computer processor measures the ambient temperature X degrees before energizing the heating element. Thereafter the computer processor energizes the heating element to a specified temperature level. Upon energizing the thermistor, the computer processor continuously measures the temperatures using the thermistor, while the heating element is energized, until such time as the temperature measured reaches Y degrees over X. For instance, Y can range from 1 C to 50 C, such as 5 C. Y can vary with X. The time to which X rises to Y is then stored and used to determine the thermal conductivity of the subsurface. At such time that the computer processor records Y degrees over X, the computer processor also deenergizes the heating element. Optionally, the computer processor further samples the temperature decay to determine a time to which the thermistor reaches ambient X.

One way to analyze the relationship between temperature rise and time, and thermal conductivity, is using the concept of thermal diffusivity. Thermal diffusivity is a material property that characterizes how quickly heat can propagate through a substance. The equation that relates temperature rise ($\Delta T$), time (t), and thermal conductivity ($\kappa$) is known as the heat conduction equation:

$$\Delta T = (\kappa \times t)/(\rho \times c)$$

Where: $\Delta T$ is the temperature rise (in degrees Celsius or Kelvin), t is the time (in seconds), K is the thermal conductivity (in units of watts per meter-kelvin, W/(m·K)), $\rho$ is the density of the material (in units of kilograms per cubic meter, kg/m$^3$), and c is the specific heat capacity of the material (in units of joules per kilogram-kelvin, J/(kg·K)). This equation shows that the temperature rise ($\Delta T$) is directly proportional to the product of thermal conductivity ($\kappa$) and time (t), divided by the product of density ($\rho$) and specific heat capacity (c). Therefore, a larger thermal conductivity or a longer time will result in a greater temperature rise, assuming other parameters remain constant. In simpler terms, if you have a material with higher thermal conductivity, heat will transfer more quickly through it, leading to a larger temperature rise for the same duration. Similarly, if you increase the time over which heat is applied to a material, the temperature rise will also be greater, given a constant thermal conductivity. This relationship assumes a one-dimensional heat conduction scenario and neglects other factors that may affect heat transfer, such as convection or radiation. In practical situations, the heat conduction equation is often solved numerically or using more complex mathematical models to account for these additional factors and provide a more accurate analysis.

In another particular embodiment, the at least one processor is configured to perform operations including at least energize the at least one heating element to emit heat for a specified period of time; de-energize the at least one heating element to stop emitting heat; and measure temperature using the at least one thermistor over time to determine a decay profile. For example, the computer processor can turn on the heating element to a specified level to heat an area of the soil for a specified time. The computer processor can sample the temperature using the thermistor and determine when the temperature has reached a certain temperature increase over ambient or is in steady-state. Thereafter, the computer processor deactivates the heating element while continuously monitoring the temperature using the thermistor. The time and temperature is monitored and recorded by the computer processor to identify a decay profile and/or time associated with return to the ambient temperature level. The decay profile is usable to determine the thermal conductivity of the subsurface.

The temperature decay profile, also known as the temperature-time curve, describes how the temperature of a material changes over time after a heat source is removed or when the material is subjected to cooling. The relationship between the temperature decay profile and thermal conductivity provides insights into how quickly heat dissipates from a material. The rate at which heat dissipates from a material is governed by Fourier's Law of Heat Conduction, which states that the heat flux (Q) through a material is proportional to the negative gradient of temperature (dT/dx) and the thermal conductivity ($\kappa$) of the material:

$$Q = -\kappa \times (dT/dx)$$

When considering a solid material with one-dimensional heat transfer, the temperature gradient (dT/dx) can be replaced with the time derivative of temperature (dT/dt). Therefore, the equation can be rewritten as:

$$Q = -\kappa \times (dT/dt)$$

In this form, the equation shows that the heat flux (Q) is directly proportional to the negative of the time derivative of temperature (dT/dt) and the thermal conductivity ($\kappa$). The negative sign indicates that heat flows from regions of higher temperature to lower temperature. When a heat source is removed, the material will start to cool down, and its temperature will decrease over time. The rate of temperature change (dT/dt) will be negative, indicating a decrease in temperature. The magnitude of the temperature decay rate will depend on the thermal conductivity of the material. If a material has a higher thermal conductivity, it can efficiently conduct heat, allowing for faster heat dissipation. As a result, the temperature of the material will decrease more rapidly over time, leading to a steeper temperature decay profile. Conversely, a material with lower thermal conductivity will have a slower heat dissipation rate, resulting in a less steep temperature decay profile. Therefore, the thermal conductivity of a material directly influences the rate at which it cools down or loses heat. A material with higher thermal conductivity will exhibit a faster temperature decay, while a material with lower thermal conductivity will have a slower temperature decay.

In another particular embodiment, at least one processor is configured to perform operations including at least energize the at least one heating element to emit heat; measure temperature using at least one two thermistors to detect a preset temperature gain above ambient; de-energize the at least one heating element to stop emitting heat; measure temperature using the at least two thermistors over time to determine at least two decay profiles; and determine a mean temperature decay index using the at least two decay profiles. The computer processor can use one or more heating elements in combination with at least two thermistors that are spaced apart. The computer processor samples temperature over time for each of the thermistors, relative to activation of the heating element, to determine a mean time to reach a specified gain above ambient and/or a mean decay profile to reach ambient. Thus, the computer processor can activate the heating element and then use thermistors to determine when each reaches a common threshold above ambient. When the thermistors flank the heating element by a specified distance, the time to reach a certain level above ambient for each thermistor can be slightly different. An average of the two rise times can therefore provide a more accurate assessment of thermal conductivity that accounts for local soil irregularities.

Using multiple temperature measurements to determine thermal conductivity offers several benefits: 1. Accuracy: Thermal conductivity is influenced by various factors such as temperature, pressure, and material composition. By taking multiple temperature measurements at different points or intervals, more data is gathered to obtain a more accurate representation of the thermal behavior of the material. 2. Spatial Variation: Materials often exhibit spatial variations in thermal conductivity due to variations in composition, density, or microstructure. By measuring temperatures at multiple locations, the system can account for spatial variations and obtain a better understanding of how thermal conductivity changes within the material. This is particularly important when dealing with heterogeneous materials or materials with complex geometries. 3. Anisotropic Materials: Some materials have different thermal conductivities in different directions. These anisotropic materials require multiple temperature measurements to determine their thermal conductivity accurately. By measuring temperatures along different axes or directions, you can capture the anisotropic behavior and calculate the corresponding thermal conductivity components. 4. Thermal Gradients: In certain cases, the thermal conductivity of a material may vary with temperature. By measuring temperatures at different levels or over a range of temperatures, you can capture the thermal gradients within the material and account for the temperature dependency of thermal conductivity. This is especially important when analyzing materials subjected to varying temperatures or temperature gradients. 5. Verification and Consistency: Multiple temperature measurements allow for cross-verification and consistency checks. By comparing the measured temperatures and the resulting thermal conductivity values, the system can ensure the reliability of the data and identify any inconsistencies or errors. This helps to validate the experimental setup, measurement techniques, and the overall accuracy of the determined thermal conductivity. In summary, with the computer processor using multiple temperature measurements, a more comprehensive and accurate assessment of thermal conductivity is provided. It allows for the consideration of spatial variations, anisotropic behavior, temperature gradients, and ensures reliable and consistent results.

In another particular embodiment, the at least one processor is configured to perform operations including at least control the at least one heating element; measure temperature using the at least one thermistor over time; and generate an output of the temperature aligned with at least one of depth, tip resistance, sleeve resistance, pore pressure, and inclination. The processor can measure CPT variables prior to, after, or during measurements of thermal conductivity at the same site and subsurface depth. The measurements such as depth, tip resistance, sleeve resistance, pore pressure, and inclination can be geolocated with the thermal conductivity measurements to establish a more comprehensive model of the subsurface characteristics. Furthermore, the processor or processors can aggregate thermal conductivity and CPT data from a plurality of sites or depths to establish a 3D matrix of geolocated data usable for a variety of scientific or industrial purposes.

Combining Cone Penetration Test (CPT) data with thermal conductivity data offers several benefits in geotechnical and thermal analysis: 1. Subsurface Characterization: CPT provides valuable information about the subsurface soil or rock layers, including their composition, density, and stratigraphy. By integrating CPT data with thermal conductivity data, the system provides a comprehensive understanding of the subsurface conditions and the thermal properties of the materials present. This helps in accurate geotechnical and thermal analysis, particularly in applications such as ground-source heat pumps, electrical energy transport, or thermal energy storage. 2. Heat Transfer Analysis: Thermal conductivity data alone provides information about how heat flows through a material. However, by incorporating CPT data, the system can assess the geotechnical properties of the subsurface and how they impact heat transfer. For example, the presence of different soil layers with varying thermal conductivities or moisture contents can significantly affect the thermal behavior of a system. By combining CPT and thermal conductivity data, the system can perform more accurate heat transfer analyses and optimize the design and performance of geotechnical and thermal systems. 3. Geothermal Applications: CPT data combined with thermal conductivity data is particularly useful in geothermal energy applications. Geothermal systems involve transferring heat between the subsurface and a heat pump or heat exchanger. By integrating CPT data, which provides information about the subsurface thermal gradient, lithology, and hydraulic properties, with thermal conductivity data, the system supports accurate models and improved designs for geothermal systems. 4. Thermal Remediation: In environmental remediation projects, where heat is applied to the subsurface to enhance the removal of contaminants, combining CPT data with thermal conductivity data enables better assessment of how efficiently heat is distributed and transferred within the subsurface. Thus, the system can enable better design and control of remediation strategies. 5. Improved Site Characterization: By merging CPT data and thermal conductivity data, the system provides a more comprehensive site characterization. This integrated approach provides a clearer understanding of the subsurface conditions, including soil or rock properties, moisture content, thermal gradients, and thermal behavior. Such detailed information is valuable in various applications, such as underground construction, foundation design, and thermal analysis for infrastructure projects.

The present invention may have additional embodiments, may be practiced without one or more of the details described for any particular described embodiment, or may have any detail described for one particular embodiment practiced with any other detail described for another embodiment.

While preferred and alternate embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. A probe comprising:
a cone penetration head configured to obtain cone penetration testing (CPT) data;
at least one heating element;
a plurality of temperature sensors, the plurality of temperature sensors being thermally insulated within the probe from the at least one heating element; and
at least one processor configured to determine thermal conductivity of material around the probe based on a mean time to rise to a specified temperature gain over ambient as measured using the plurality of temperature sensors.

2. The probe of claim 1, wherein the cone penetration head includes one of more of the following types of sensors: pore pressure or friction.

3. The probe of claim 1, wherein the processor is further configured to:
activate the at least one heating element;
detect a temperature gain above ambient using the plurality of temperature sensors;
deactivate the at least one heating element in response to the temperature gain above ambient; and
determine thermal conductivity based on a temperature decay profile.

4. The probe of claim 1, wherein the at least one heating element comprises a plurality of heating elements.

5. The probe of claim 1, wherein the plurality of temperature sensors are thermally insulated using one or more of the following materials: PI, PEEK, PPS, PEI, or PTFE.

6. The probe of claim 1, wherein the cone penetration head is removably coupled to the probe.

7. A probe attachment device comprising:
at least one heating element;
a plurality of temperature sensors, the plurality of temperature sensors being thermally insulated within the probe attachment device from the at least one heating element; and
at least one processor configured to determine thermal conductivity of material around the probe attachment device based on a mean time to rise to a specified temperature gain over ambient as measured using the plurality of temperature sensors,
wherein the probe attachment device is configured to removably couple to a cone penetration head configured to obtain cone penetration testing (CPT) data.

8. A device, the device comprising:
a cone penetration head including one of more sensors;
at least one heating element;

a plurality of temperature sensors, the plurality of tem-
  perature sensors being thermally insulated within the
  device from the at least one heating element; and
at least one processor configured to determine thermal
  conductivity of material around the probe based on a
  mean time to return to ambient temperature from a gain
  over the ambient temperature as measured using the
  plurality of temperature sensors.
  9. The probe of claim 1, wherein the at least one processor
is further configured to geolocate the CPT data with thermal
conductivity data.
  10. The probe of claim 1, wherein the at least one
processor is further configured to establish a 3D model of the
CPT data and thermal conductivity data correlated to a
particular GPS position within a subsurface.
  11. The probe of claim 1, wherein the at least one heating
element comprises:
at least one heating disk segment.
  12. The probe of claim 1, further comprising:
one or more spacers usable to position the plurality of
  temperature sensors at different positions along a length
  of the probe.
  13. The probe of claim 1, wherein the at least one
processor is physically integrated into the probe.
  14. The probe of claim 1, wherein the at least one
processor is physically separate from the probe and linked
via a wired connection.
  15. The probe of claim 1, wherein the at least one
processor is physically separate from the probe and linked
via a wireless connection.
  16. The probe of claim 1, wherein the at least one
processor is configured perform the following operations to
determine thermal conductivity of material around the
probe:
measure ambient temperature using at least one of the
  plurality of temperature sensors;

energize the at least one heating element;
measure temperature using the plurality of temperature
  sensors to determine the mean time to rise to the
  specified gain over the ambient temperature; and
determine thermal conductivity based on the mean time to
  rise.
  17. The device of claim 8, wherein the at least one
processor is physically integrated into the device.
  18. The device of claim 8, wherein the at least one
processor is physically separate from the device and linked
via a wired connection.
  19. The device of claim 8, wherein the at least one
processor is physically separate from the device and linked
via a wireless connection.
  20. The device of claim 8, wherein the at least one
processor is further configured to:
energize the at least one heating element;
measure temperature using the plurality of temperature
  sensors to determine a mean time to rise to the gain
  over the ambient temperature; and
determine thermal conductivity based on the mean time to
  rise.
  21. The device of claim 8, wherein the at least one
processor is configured to perform the following operations
to determine thermal conductivity of material around the
probe:
energize the at least one heating element to emit heat;
de-energize the at least one heating element to stop
  emitting heat in response to detecting the gain over the
  ambient temperature;
measure temperature using the plurality of temperature
  sensors to obtain a set of times to return to the ambient
  temperature; and
determine thermal conductivity based on the mean of the
  set of times to return to the ambient temperature.

* * * * *